United States Patent [19]
Nemirow

[11] Patent Number: 5,528,933
[45] Date of Patent: Jun. 25, 1996

[54] DYNAMIC VOLUMETRIC INSTRUMENT GAUGE

[76] Inventor: Daniel M. Nemirow, 6812 157th Pl. SW., Edmonds, Wash. 98020

[21] Appl. No.: 152,847

[22] Filed: Nov. 15, 1993

Related U.S. Application Data

[63] Continuation-in-part of Ser. No. 528,921, May 25, 1990, Pat. No. 5,261,274.

[51] Int. Cl.$^6$ ........................................... G01F 17/00
[52] U.S. Cl. .................................. 73/149; 73/579
[58] Field of Search .................... 73/149, 579, 290 V, 73/580; 367/908

[56] References Cited

U.S. PATENT DOCUMENTS

| | | | |
|---|---|---|---|
| 2,666,326 | 1/1954 | Poole et al. | 73/579 |
| 4,535,627 | 8/1985 | Prost et al. | 73/149 |
| 4,811,595 | 3/1989 | Marciniak et al. | 73/149 |

*Primary Examiner*—Hezron E. Williams
*Assistant Examiner*—Nashmiya N. Ashraf
*Attorney, Agent, or Firm*—J. Michael Neary

[57] ABSTRACT

An instrument having a transducer and a sensor that are mounted on the exterior surface of a liquid container or tank. The transducer is tuned by electronic signals to the mechanical resonant frequency of the liquid container or tank. The sensor converts the mechanical vibrations into dynamic electrical signals using electronic components. A phase detector and feedback circuitry force the transducer to track the resonant frequency of the tank as liquid is removed from the tank. The signal output of the feedback control circuitry is converted to display the amount of liquid remaining in the tank. The resonant frequency of the liquid container is a measure of the total mass of the container. This includes the tare weight of the container plus the weight of the liquid in the tank. At resonance the amplitude response of the tank is much larger than the noise of the environment. As the intelligence of the instrument to interpret changes in liquid volume is a function of frequency, this adds to the noise immunity. The nonlinear dynamic response of the instrument is an asset in the use of this gauge for fuel tanks and other applications.

13 Claims, 8 Drawing Sheets

FIG. 9

DYNAMIC VOLUMETRIC INSTRUMENT GAUGE

RELATIONSHIP TO PRIOR APPLICATIONS

This application is a continuation-in-part of patent application No. 07/528,921, filed May 25, 1990 now U.S. Pat. No. 5,261,274 issued on Nov. 16, 1993.

BACKGROUND

1. Field of Invention

This invention relates to gauges for measuring liquid volume in liquid containers and tanks. More particularly, the invention relates to a dynamic gauge that uses signals that permit the installation of transducers and/or sensors on the outside surface of the containers.

2. Description of Prior Art

Other systems use capacitance probes, float actuated electro-mechanical devices, or differential pressure sensors immersed in the fluid. Ultrasonic transducer systems have been inserted in the top of liquid tanks to measure liquid level. Similarly, acoustic systems have used transducers inserted in the tank to measure the volumetric change as fluid is removed from a tank. Strain gauges have been used on the exterior of the tank to measure the liquid weight or the volume of liquid remaining in the tank. Exterior mounting, or non-invasiveness, is obviously a desirable attribute, but strain gauges are expensive and have reliability problems even in environments that are only moderately hostile. All invasive systems, i.e. those that require the sensor or transducer to be inserted in the liquid container, have higher installation costs and usually are relatively unreliable, more expensive, and require more maintenance. These systems do not lend themselves to multi-tank applications easily.

Transducers, even ones that I expected to work accurately and repeatably in test, would often perform satisfactorily for awhile, and then would unaccountably degrade in performance. On inspection, the transducers appeared to be normal, but their performance was erratic. Such performance would be unacceptable in many of the intended applications, such as truck and marine fuel tanks, so it was necessary to discover and eliminate the cause of the erratic transducer performance, which I have done.

SUMMARY OF THE INVENTION

An object of this invention is to provide an improved configuration of liquid volumetric instrument gauge. Another object of this invention is to provide an improved volumetric gauge for liquids in a tank that provides an improvement in reliability, repeatability, maintainability, and cost of installation, and also provides easier, faster installation and initial adjustment design over that of the present competitive gauges. Yet another object of this invention is to provide an improved liquid volume gauge having a transducer and sensor that can be mounted on the exterior of the tank to measure the liquid weight or the volume of liquid remaining in the tank. Another still further object of this invention is to provide an improved fuel volume gauge that functions reliably in a noisy environment, with increasing accuracy as the remaining volume of fuel decreases. An additional still further object of the invention is to provide an improved unitary transducer/sensor, for use with a volumetric liquid gauge, that is accurate and provides consistent, repeatable performance over extended periods of time.

These and other objects of the invention are attained in several preferred embodiments of the invention wherein an electrical signal is applied to a transducer, mechanically coupled to the liquid tank, to excite a structural vibration in the tank at the loaded structural resonant frequency. A sensor on the tank picks up the vibration and produces an electrical signal representative of the amplitude and frequency of the structural vibrations of the tank. Electronic circuitry interprets signal from the sensor to detect the resonance frequency and translates it in terms of the liquid volume remaining in the tank. Another embodiment produces a mechanical pulse on the tank, to which the tank structure responds with a damped transient signal whose frequency is a function of the total mass of the tank and its liquid load, thus providing another technique for measuring the fluid remaining in the tank.

For analysis and test, three different liquids were considered: gasoline, diesel fuel, and water. However, since the disclosed system depends on the change in weight of the tank as liquid is removed, the system will work equally well with other liquids also.

Several types of transducers were evaluated for exciting the tank into mechanical resonance. Magnetostrictive, piezoelectric, sonar thumper, and moving coil transducers were analyzed for the major market requirements. All may be used for a variety of applications, but the magnetostrictive, piezoelectric, and moving coil transducers have been tested. The magnetostrictive devices will be described because of their high reliability under adverse environmental conditions.

A sinusoidal or pulse electrical signal applied to a wire coil wound around a magnetostrictive material will change the dimensions of the material to produce the vibration or pulse, respectively. The "initial conditions" on the transducer are the conditions to which the transducer is subjected to at the time at which the initial signal is impressed. I have discovered that these initial conditions greatly affect the response of the transducer to the impressed signals, so to remove this cause of chaotic response and create the conditions for a consistent and repeatable response from operation of the transducer for extended periods of use, I set the initial conditions on the transducer before impressing the signal. Setting the initial conditions on the transducer militates for consistent transducer performance despite the presence of varying environmental conditions which otherwise tends to affect the transducer performance.

DETAILED DESCRIPTION OF THE PREFERRED EMBODIMENTS

Figure 1:
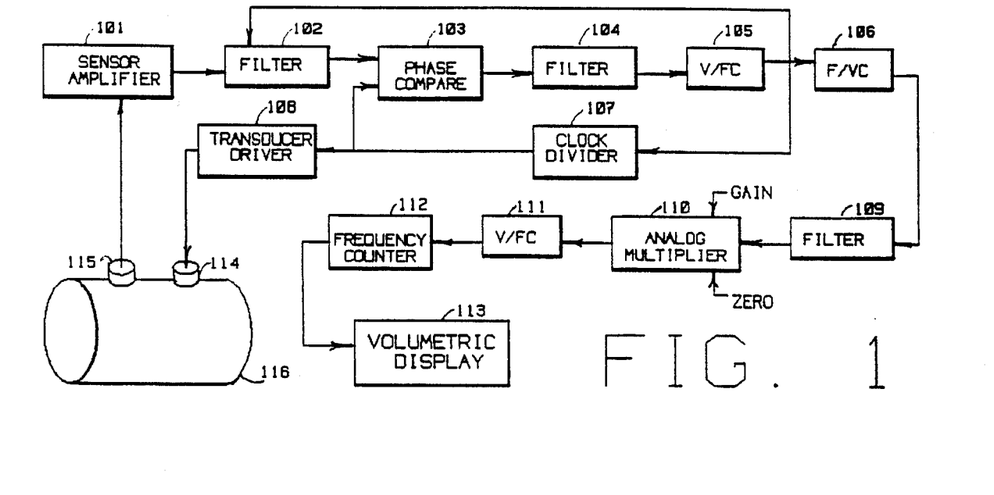
FIG. 1 is a schematic diagram of a preferred embodiment of this invention.

Turning now to the drawings, wherein like reference characters designate identical or corresponding components, and more particularly to FIG. 1 thereof, a first embodiment of this invention is illustrated having a transducer 114 and a sensor 115 mounted on the exterior surface of a tank 116. The transducer imparts mechanical excitation of the tank structure along a primary axis of action, and the sensor picks up the structural vibration of the tank and produces an electrical signal to the electrical circuit which detects the structural resonant frequency of the tank and its liquid load. The electronic circuitry provides the data manipulation to display on a volumetric display 113 the volume of fluid remaining in the tank 116 based on the resonant frequency of the tank, which is a function of its liquid load.

One aspect of this invention includes automatically tuning the transducer driver to operate at the resonant frequency of the tank, which is an analytic inverse exponential function of the volume of fluid remaining in the tank. Phase locked loop feedback control circuitry forces the transducer to change its frequency as the tank empties and track the resonant frequency received by the sensor. This invention is also unique in that dynamic rather than static measurement techniques are used. Strain gauges are considered static devices. The transducers and sensors used in this invention are dynamic devices. Dynamic signals can be defined as those signals which vary as a function of time and the intelligence is in the frequency of the signal.

FIG. 1 displays the general design for a single tank system. The box elements in the circuits shown in the drawings are not shown in detail because they are all conventional off-the-shelf items known to those skilled in the art. The sensor 115 sends its dynamic signals to a suitable amplifier, which, in the case of a piezoelectric sensor would be a charge amplifier 101. The charge amplifier circuitry includes a bandpass filter and a line driver. The circuitry ot the charge amplifier 101 drives a switched capacitor filter 102 which is controlled by the output of a voltage-to-frequency converter 105 and delivers its output to a phase detector 103. The phase detector 103 drives a filter 104 which, in turn, drives the voltage-to-frequency converter 105. The VFC 105, through a divide-by-100 circuit 107 (also known as a "clock divider"), closes the loop to the phase detector 103 and drives a transducer driver 108 which drives the transducer to vibrate the tank at its resonance frequency. The VFC 105 drives a frequency-to-voltage converter 106 which, through a filter 109, drives an analog multiplier 110.

The analog multiplier 110 can be configured to provide the inverse square root of an analog value. Since the resonant frequency of the tank is an inverse square root function of its mass, the analog multiplier can be configured to provide the required function of converting resonant frequency to mass. The output of the analog multiplier is converted from an analog signal back to a frequency signal in V/FC 111. These circuits convert the structural resonances to frequencies that drive a volumetric display 113 through a counter 112.

The ZERO and SPAN (or GAIN) adjustments, which in practice would be made to the analog multiplier 110 in the linearize circuits permit a single system design to cover a wide range of applications. Similarly, the linearize circuits will permit application to a wide range of liquid container configurations.

For many applications, a magnetostrictive component may be used as the transducer. This type of transducer changes its physical dimensions under the influence of a change in magnetic flux. My tests have shown that this type of a transducer provides an excellent method of transmitting vibrations into a mechanical structure. A piezoelectric film type component is useful as the sensor 115 for some applications. This is a low cost, reliable, and easily installed component.

Figure 2:
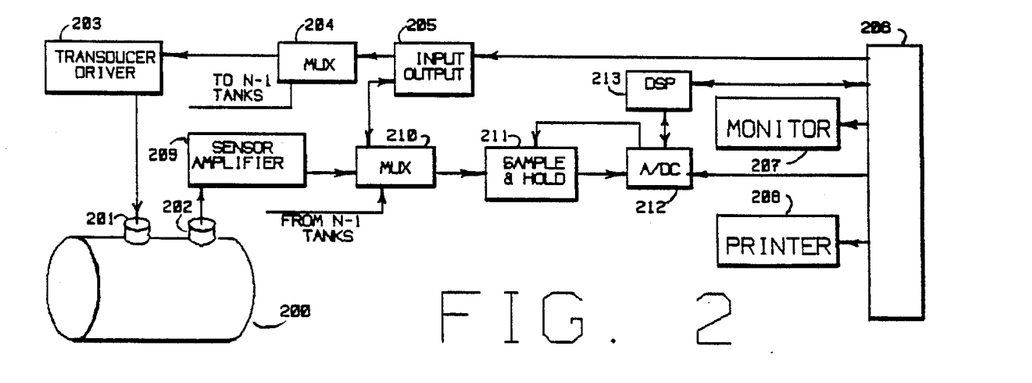
FIG. 2 is a schematic diagram of a second embodiment of the invention to meet the requirements of acquiring volumetric data from a multi-tank system.
Figure 4A:
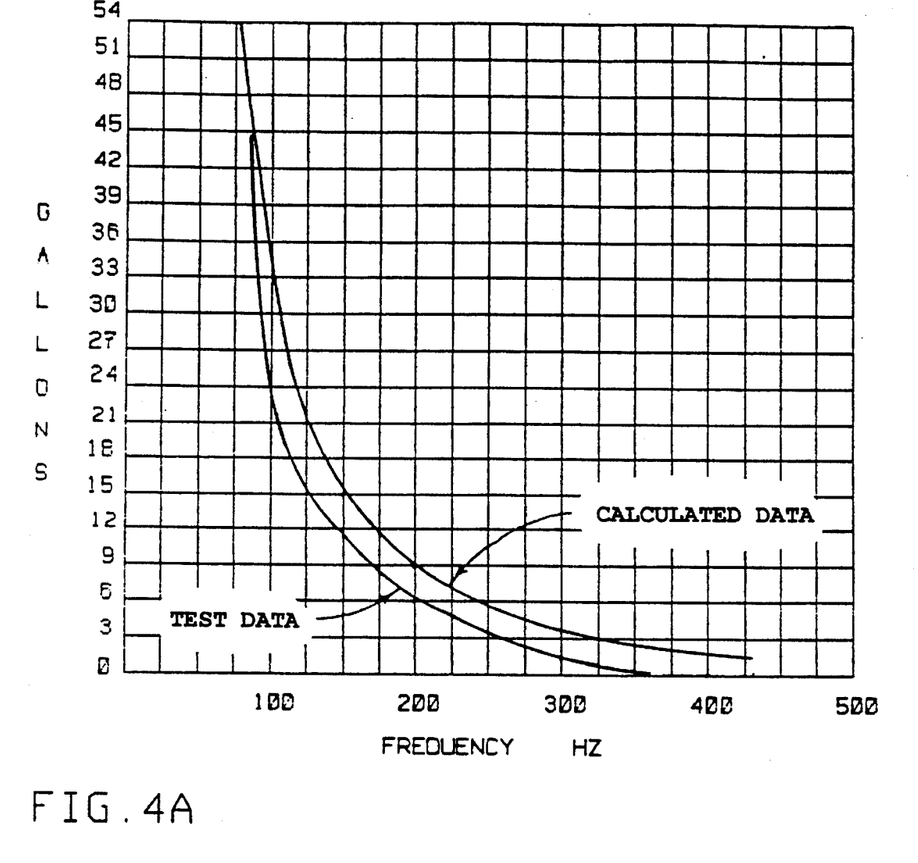
FIG. 4A is a graph illustrating the acquired test data, and calculated data for a typical fuel tank.

FIG. 2 illustrates in schematic form the circuitry required for measuring the liquid remaining in a plurality of tanks. These tanks may report sequentially their tank content or upon interrogation annunciate their content. A desk top computer 206 is augmented with interface cards containing date acquisition, digital signal processing, and multiplexing components, and software functions track the required data. An elapsed time clock in the computer provides the time when each tank is interrogated. The software, interface hardware, and computer memory provide the closed loop control and displays required in many applications. "ZERO" and "SPAN" (or "GAIN") adjustments, corresponding to the similar adjustments described for FIG. 1, are readily incorporated in the computer memory. As the intrinsic data is exponential, the accuracy improves exponentially as the tank is emptied. This improves the accuracy of liquid flow information acquisition at low levels of liquids. For many fuel tank applications this is a requirement, and FIG. 4A illustrates the improvement in accuracy as the remaining fluid decreases. The number of tanks is limited only by the time required to reliably annunciate the quantity of liquid remaining in each tank. To improve the reliability in a noisy environment, digital filtering and averaging techniques are employed.

As this invention describes a volumetric gauge, the shape of the tank is irrelevant. The only structural requirements of the tank are that the material have relatively high stiffness and low dampening. Steel, aluminum, and fiberglass tanks usually qualify. A sensor 202, shown in FIG. 2, is required for each tank. An amplifier 209 interfaces between the sensor 202 and a multiplexer (MUX) 210. A transducer driver 203 drives a transducer 201. All other components are at the computer location. A multiplexer (MUX) 204 routes the correct driving signal to the required tank through the driver 203. An input-output component 205 couples the signal from the computer to the multiplexer 204. The computer 206 stores the acquired data in its memory, displays the data on is monitor 207, and prints data on the printer 208. The multiplexer 210 receives the dynamic data from each of the tanks upon command from the computer interface 205. Sequentially, the sample and hold component 211 receives the dynamic data from its multiplexer 210 and delivers it upon command to the analog to digital converter 212. The A/DC 212 receives its sampling frequency from the computer 206. The A/DC provides a digital signal processer (DSP) 213, and ultimately the computer, a digital block of data defining the frequency of the structural vibration as a function of the liquid remaining in the tank. The DSP 213 provides all the necessary filtering and mathematical computations to meet a variety of requirements. These may include transform mathematics, correlation as a form of tone decoding, digital filtering, and linearization of data for display and recording. The DSP component is shown external to the computer to emphasize its importance. It is usually assembled within the computer.

Figure 3:
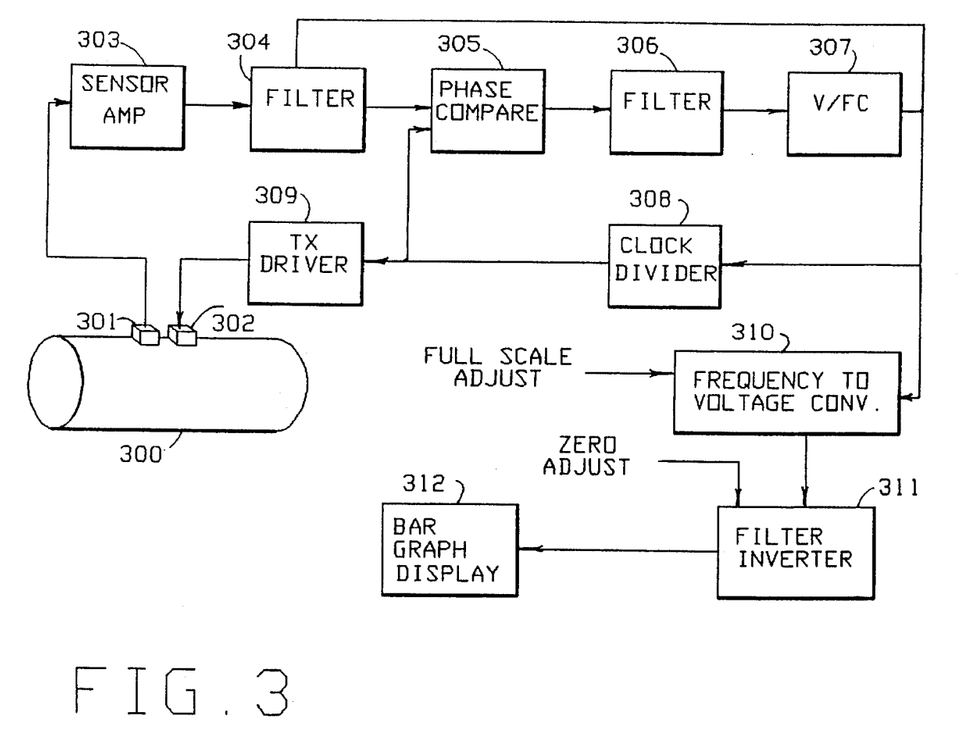
FIG. 3 is a schematic diagram of a third embodiment of the invention, showing a low cost volumetric gauge instrument.

FIG. 3 illustrates, in schematic form, a low cost embodiment of this invention. From the tank 300 to the voltage-to-frequency converter (V/FC) 307 the circuitry and components are identical to that of FIG. 1. The output of the V/FC 307 sends its resonance signal to the frequency-to-voltage converter 310. This component has a span adjustment, also known as a gain or full scale adjustment. The direct current voltage output of this component is connected to a filter inverter 311. This component has a zero adjustment. The output of the filter invertor 311 is then connected to the input of a conventional display device, such as an analog meter 312 or bar graph display. Analysis of the consumer, marine and industrial market requirements have shown that the inverse exponential response of this instrument to be an advantage. The accuracy of reading increases exponentially as the fluid volume decreases. This is interesting to marine vessel operators on long voyages.

FIG. 4A is a graphical plot of the functional relationship between the resultant resonant frequency of the tank and the volume remaining in the tank. The frequency is considered the dependant variable. The volume of the fluid in the tank is considered the independent variable. This is justified as the fluids used in the tanks are relatively incompressible. Also, mass is related to volume through a constant multiplier. The "ZERO" and "SPAN" adjustments compensate for all constant value considerations. From the dynamics equation of motion:

$$Fo = M\ddot{x} + C\dot{x} + Kx$$

Fo is defined as a force developed by an electrical signal applied through a transducer which drives the loaded structure (tank) of mass M to mechanical resonance. C is defined as the dampening coefficient and is considered small for a tank of stiff material. K is defined as the stiffness of the structure. As the dampening coefficient is considered small and the stiffness is considered constant over the range of measurements:

$$Fr = \sqrt{K/M} = \sqrt{1/M} = K'' \sqrt{1/G}$$

Fr is defined as the resonant frequency of the tank in Hz. M in this equation is the mass of diesel fuel at 57.2 pounds per cubic foot. K' in this equation is combined with other constants. K" is defined in this equation to convert mass to gallons. K" is the one parameter that is adjustable to meet the requirements of a wide variety of tanks. The "ZERO" adjustment compensates for the tare weight of the tank. The "SPAN" adjustment provides calibration of the full tank.

Figure 4B:
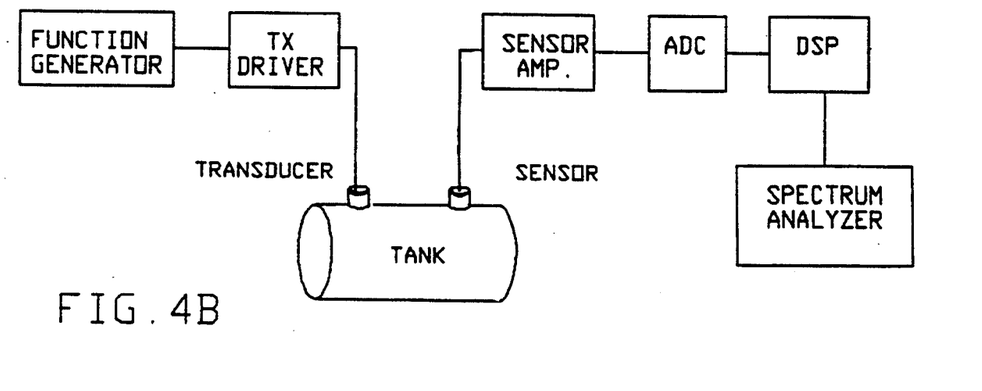
FIG. 4B is a schematic diagram of the test setup used to acquire the data illustrated in FIG. 4A.

FIG. 4B is a schematic diagram of the circuit used to acquire the data depicted in FIG. 4B. It is essentially a simplified version of the circuit shown in FIG. 2 but without the feedback from the sensor to track the tank resonance frequency, since that function is performed by the function generator.

Figure 5:
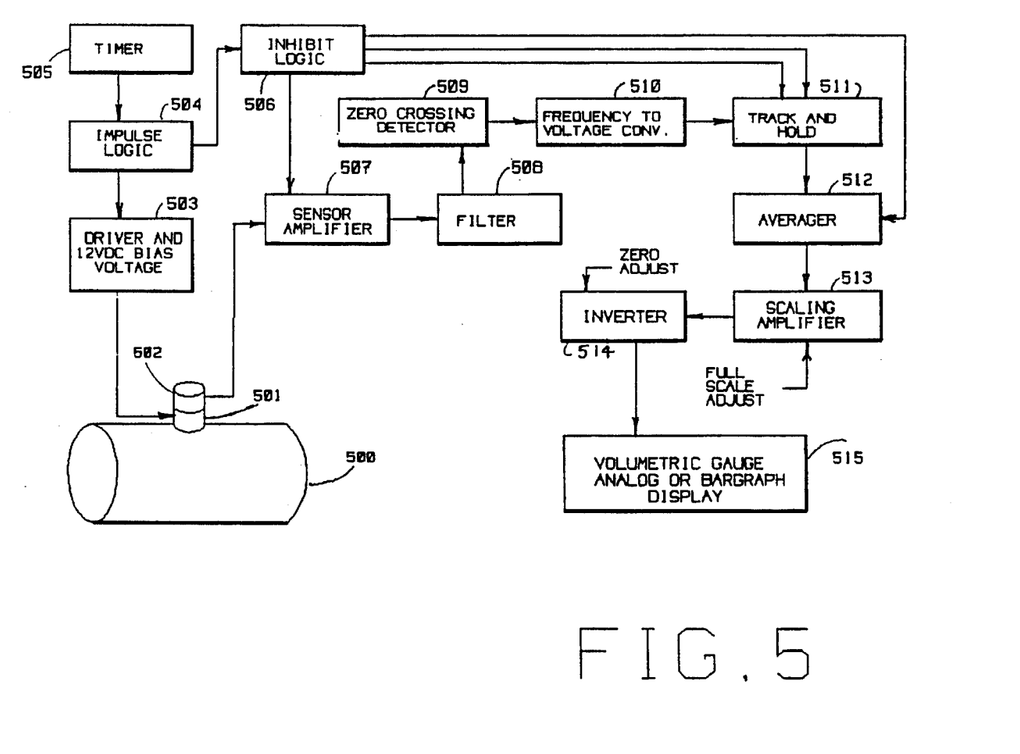
FIG. 5 is a schematic diagram of a fourth embodiment of the invention, showing a high noise immunity instrument.

FIG. 5 illustrates data acquisition circuitry that provides the necessary high noise immunity required in many applications. This embodiment improves reliability and forces the burden of capability into the design of the electronic circuitry. A transducer driver 503 delivers narrow impulses to a transducer 501 and a bias current from a voltage source. An impulse logic circuit 504 generates these impulses under control of a timer 505. The impulse logic circuit 504 also controls the inhibit logic circuit 506 which delays the response of the amplifier 507 for a predetermined time after the impulse to the tank 500. The inhibit logic 506 also precludes the operation of a track and hold circuit 511 for a predetermined time. An averager circuit 512 is also controlled for another period of time by the inhibit logic 506.

The amplifier 507 receives a resonant periodic transient signal from sensor 502. A band pass filter 508 delivers this filtered signal to the zero crossing detector 509. The zero crossing detector 509 and the frequency-to-voltage converter 510 deliver a direct current voltage signal to the track and hold circuitry 511. The signal is a function of the frequency of the transient signal and is invariant with the voltage amplitude of the frequency. The track and hold circuitry 511, under control of the inhibit logic 506, is only limited in hold time by the digital control of the timer 505, impulse logic 504, and inhibit circuitry 506. The averager 512 can accept a number of DC level voltages from the:track and hold 511 and provide their average value to the scaling amplifier 513. Zero and span adjustments are provided on this amplifier and its inverter 514. As the relationship between the liquid remaining in the tank and the analog signal is an inverse function, the inverter 514 may be required as the last circuit to drive the volumetric gauge 515.

FIG. 5 illustrates different circuitry from the other figures and shows the sensor and transducer in close proximity to each other. This provides the capability of assembly of the sensor and transducer in one package. Note also that the transducer 501 also requires a current bias to establish the initial condition of the transducer. It is important that all initial conditions be established, otherwise singularities would be measured which are not a function of the remaining fluid in the tank. Similarly, the sensors circuitry is inhibited by a fixed time to preclude erroneous responses due to the setting of the initial conditions.

Figure 6:
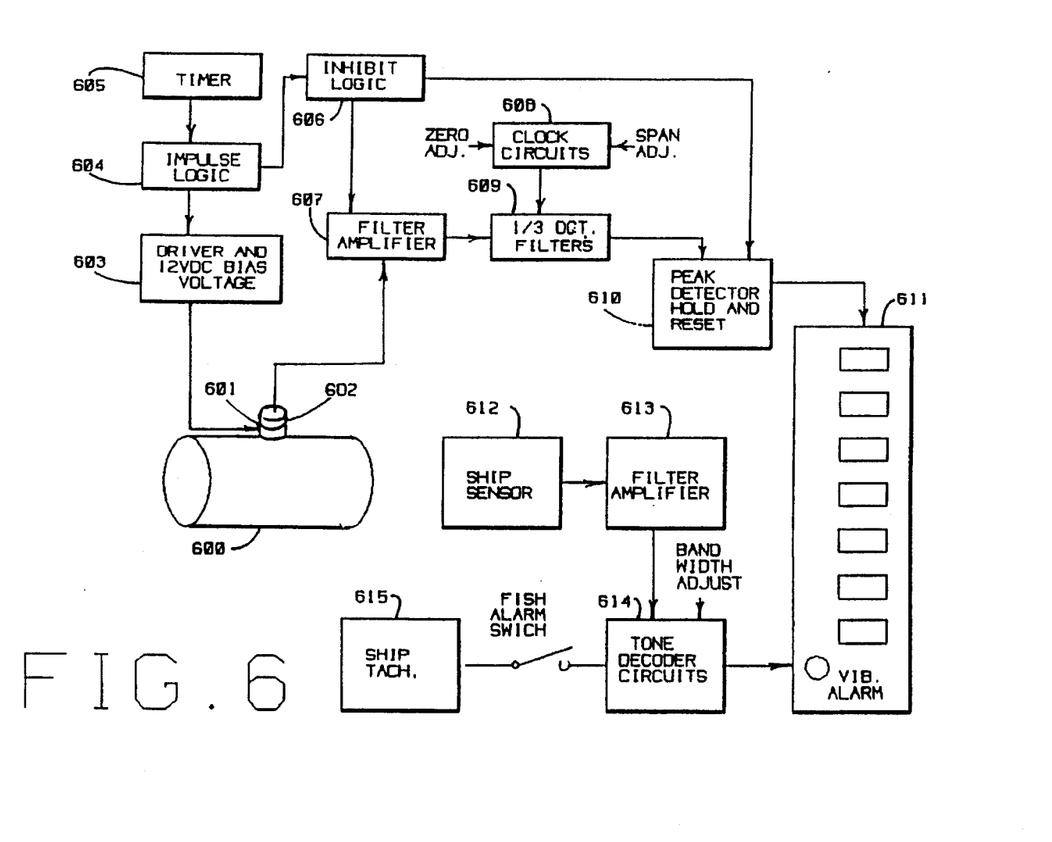
FIG. 6 is a schematic diagram of a fifth embodiment of this invention meeting some of the requirements that are unique to the marine markets.

FIG. 6 illustrates another preferred embodiment of the invention that will satisfy several marine instrumentation requirements. This embodiment is similar to that of FIG. 5 from the tank 600 to the filter amplifier 607. A series of cascaded ⅓ octave filters 609 provides a novel and low cost way to annunciated the volume of fuel remaining in the tank. Tone decoder circuits and a track and hold circuit may be substituted for the filters 609 and the peak hold detector 610.

The filters 609 receive their analog input from filter amplifier 607 and are controlled by the clock circuits 608. Filter 609 delivers one of nine signals to the peak detector 610. The peak detector similarly sends a signal to the display 611, identifying the liquid remaining in the tank. An alarm is annunciated when the liquid drops below a certain level by flashing both the 0 and gallon level lights. Components 612 to 615 permits annunciation of alarms when the signature vibrations of the engine or vessel controls are outside the normal range of frequencies for various speeds. Also, an alarm may be selected when vibrations are present in the water that alarm fish. Sensor 612 is a separate sensor that is frequently mounted on the rudder post. This sensor is amplified by 613 and drives the tone decoder circuits 614. If the fish alarm switch is closed, the tachometer 615 provides a signal to the tone decoder circuits 614 that control the annunciation of an alarm as a function of engine speed.

Figure 7:
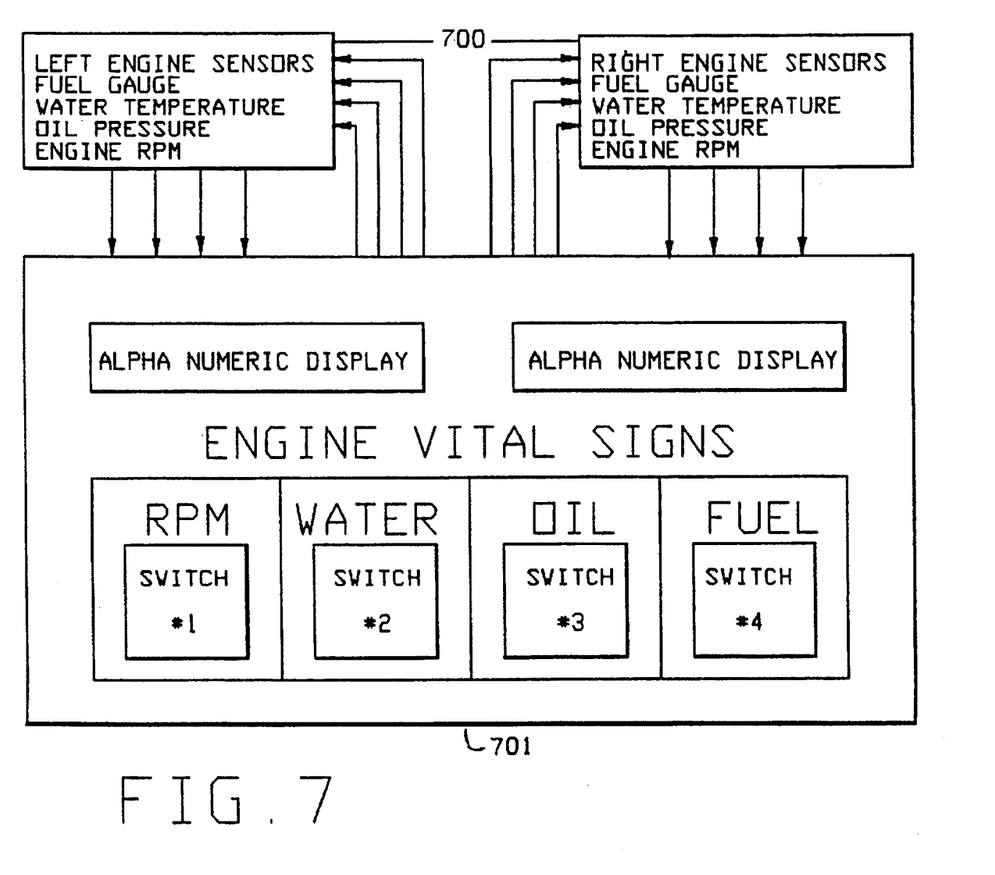
FIG. 7 is a schematic diagram of a sixth embodiment of the invention showing an arrangement for augmenting the usual instrumentation requirements of marine engines with a fuel gauge.

FIG. 7 illustrates an embodiment of instrumentation for dual marine engines. The instrumentation includes static quantity parameters such as temperature and pressure, and also includes the volumetric fuel gauge which is a dynamic measurement device. All the sensor and transducer data is controlled by a multiplexer 700. The multiplexer receives address information from one of the four momentary contact switches on the front panel. Both front panel readouts are frequency counters. Frequency decoders provide alarm annunciation. The panel display 701 illustrates the operational panel.

Figure 8:
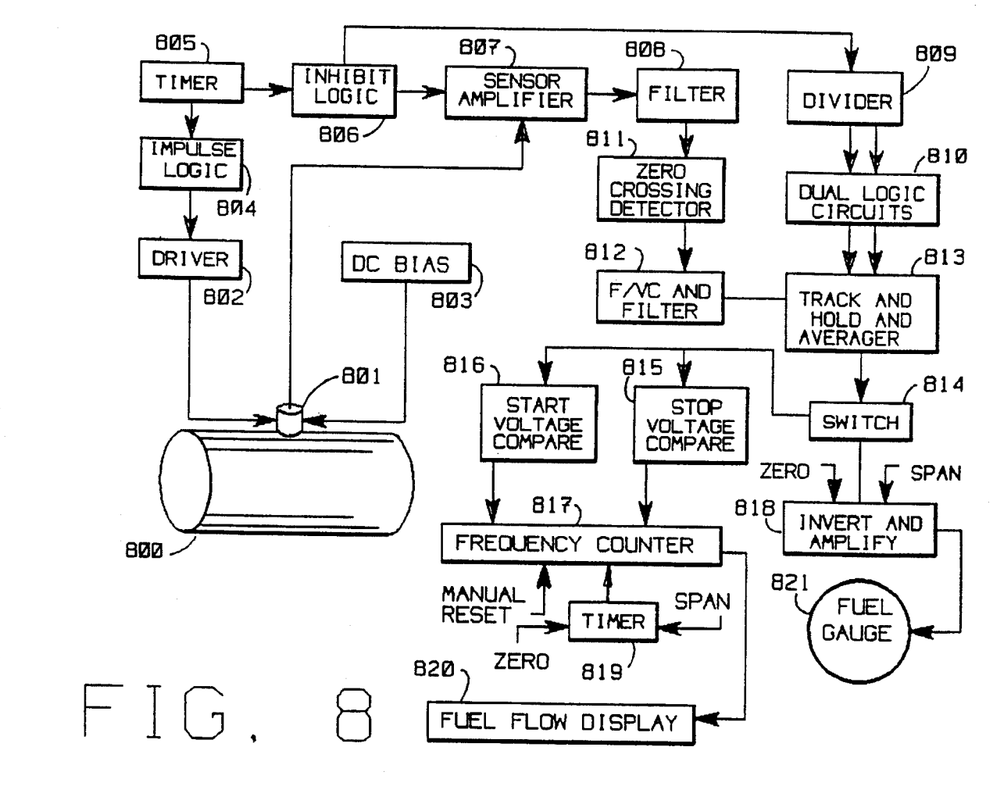
FIG. 8 is a schematic diagram of a seventh embodiment of the invention, similar to FIG. 5; but, containing dual displays of fuel flow and liquid remaining.

FIG. 8 illustrates an embodiment of this invention, similar to FIG. 5, but containing circuitry that enable the display of a dual display: fuel flow and liquid remaining. This embodiment is similar to FIG. 5 from the tank 800 to the analog display 821. The flow data acquisition and display is under operator control by a switch 814 in the output of the averager track and and hold circuitry. The flow system will start to accumulate flow data and annunciate gallons per hour when the fuel is down to 10 percent of capacity. A dual scale analog may be substituted with similar electronics for a lower cost instrument.

When the operator controlled switch 814 is in the flow position the start comparator 816 will compare the DC voltage output from the track and hold output 813 against a predetermined voltage level equivalent to 25 percent of fluid volume remaining in the tank. With a logic level signal, the start voltage compare 816 enables the start of the frequency counter 817. The counter 817 will now start counting the logic pulses provided by the timer 819. When the signal to the stop comparator is equal to the voltage representing 10 percent of volumetric capacity, the stop comparator 815 will trip. Then, the flow counter 817 will stop counting and the the fuel flow 820 will display the flow per unit of time determined by the timer 819 until manually reset. If desired, switch 814 is reset to its former operation as a volumetric gauge. If a mileage input is available or a tachometer signal, the fuel flow display can measure the fuel flow in miles per gallon by the use of a digital divider.

Figure 9:
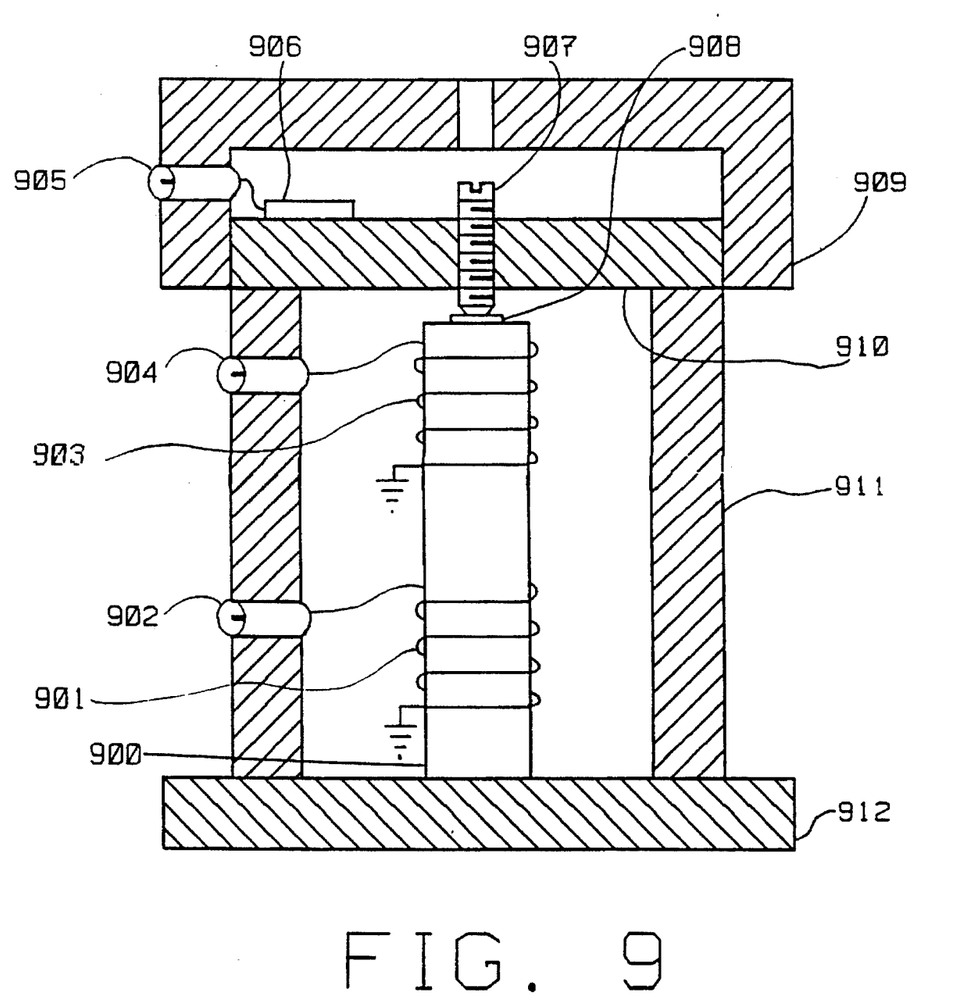
FIG. 9 is a cross section of a transducer and sensor assembled as one component for use in the embodiments of FIGS. 5, 6 and 8.

FIG. 9 illustrates the combined transducer and sensor component shown in FIGS. 5, 6, and 8. The transducer 900 is either cylindrical or tubular magnetostrictive metal, such as nickle 200. Two coils are wound on this cylinder. A direct bias current coil is connected to ground and an external source of DC current through connector 902. This DC current is adjusted to establish the initial conditions of magnetic flux, so that the chaotic results due to the initial conditions of the magnetic material and its configuration are minimized. The other coil on the transducer is the excitation coil 903. This coil receives either a pulsed or a sinusoidal signal through connector 904. A frequency sensor 906 is mounted on the structure of the unit and may be an accelerometer, magnetic, or piezoelectric component and it must be assembled in such a manner that the magnetic flux of the transducer is orthogonal to its own field and is not coupled into the sensor. The sensor 906 senses structural vibration signals and sends electrical signals through its connector 905. A set screw 907 provides the initial condition of stress through a washer 908; thereby setting the initial condition of strain on the transducer. This washer is made of a material, such as stainless steel, that has a high reluctance to magnetic flux and prevents saturation through the low magnetic reluctance paths surrounding the magnetostrictive transducer 900. These paths consist of the structural elements 910, 911, and 912. A nonmagnetic or plastic cap 909 may be used as a top cover of the transducer sensor component assembly.

Obviously, numerous modifications and variations of the preferred embodiments described herein will occure to those skilled in the art. It is expressly to be understood that these modifications and variations, and the equivalents thereof, may be practiced while remaining within the spirit and scope of the following claims, wherein

I claim:

1. An apparatus for holding liquid and measuring the volume of liquid held, comprising:

a) a transducer having a system for establishing initial conditions, including:

a magnetostrictive element having a primary axis of action;

a bias coil wound on said magnetostrictive element and having a coil axis substantially aligned with said primary axis of action;

an excitation coil wound on said magnetostrictive element and having a coil axis substantially aligned with said axis of action;

a first conductor connecting said excitation coil to an electrical signal source for applying a magnetic field to said magnetostrictive element;

a second conductor connecting said bias coil to an electrical power supply for providing a bias current to said bias coil to provide a magnetic field for establishing initial conditions of magnetic flux in a magnetic circuit through said magnetostrictive element to ensure repeatable operation for extended periods of use;

b) a liquid holding tank to which said transducer is attached for vibrating said liquid holding tank at a dynamic structural resonant frequency of said liquid holding tank in response to electrical signals which are impressed on said transducer at said structural resonant frequency as a function of the mass of a liquid load in said liquid holding tank;

c) a circuit for measuring the dynamic structural resonant frequency of said liquid holding tank loaded by said liquid load in said liquid holding tank;

d) circuitry for producing dynamic electrical resonant signals indicative of said structural resonant frequency;

e) a translating circuit for translating said dynamic resonance signals into signals indicative of said liquid load in said liquid holding tank; and f) a display electrically connected to said translating circuit for displaying the volume of said liquid load in said liquid holding tank.

2. An apparatus as defined in claim 1, further comprising:

a mechanical structure around said magnetostrictive element;

a compressive device mounted on said mechanical structure for exerting an adjustable compressive load on said magnetostrictive element to establish initial conditions of compressive stress in said magnetostrictive element to ensure repeatable operation for extended periods of use.

3. An apparatus as defined in claim 2, further comprising:

a spacer made of high reluctance material between said compressive device and said magnetostrictive element for limiting the flux density in said magnetic circuit to prevent saturation of said magnetic circuit.

4. An apparatus as defined in claim 2, wherein:

said compressive device includes a screw threaded into a hole in said mechanical structure and axially aligned with said primary axis of action, whereby said screw can be torqued down to apply compressive load on said magnetostrictive element to establish said initial conditions of compressive stress therein.

5. An apparatus as defined in claim 1, further comprising:

a flow data acquisition circuit for comparing a liquid load in said tank at a start time with a liquid load after a certain period of time has elapsed from said start time, during which elapsed time liquid has flowed out of said tank, and calculating the reduction in liquid load due to said outflow during said elapsed time to determine the flow rate out of said tank during said elapsed time.

6. A liquid volume gauge for measuring liquid volume in a tank having a structure with a structural resonant frequency that is unique for every different liquid load in said tank, comprising:

a sensor and a transducer, combined into one sensor-transducer unit and having structure mechanically fastening said unit to said tank to provide mechanical vibrations between said structure of said tank and said sensor-transducer unit, said sensor-transducer unit including:

a magnetostrictive element having a primary axis of action;

a bias coil wound on said magnetostrictive element and having a coil axis substantially aligned with said primary axis of action;

an excitation coil wound on said magnetostrictive element and having a coil axis substantially aligned with said axis of action;

a first conductor connecting said excitation coil to an electrical signal source for applying a magnetic field to said magnetostrictive element, and;

a second conductor connecting said bias coil to an electrical power supply for providing a bias current to said bias coil to provide a magnetic field for establishing initial conditions of magnetic flux in a magnetic circuit through said magnetostrictive element to ensure repeatable operation for extended periods of use;

a source of electrical signals connected to said transducer for vibrating said tank at said structural resonant frequency of said tank as a function of the mass of liquid load in said tank;

a circuit for measuring the dynamic structural resonant frequency of said tank loaded by said liquid in said tank;

circuitry for producing dynamic electrical resonant signals indicative of said structural resonant frequency;

a translating circuit for translating said dynamic resonance signals into signals indicative of said liquid load in said tank; and a display electrically connected to said translating circuit for displaying said volume of said liquid load in said tank.

7. A liquid volume gauge as defined in claim 6, further comprising:

a flow data acquisition circuit for comparing a liquid load in said tank at a start time with a liquid load after a certain period of time has elapsed during which time liquid has flowed out of said tank at an average flow rate causing a reduction in liquid load in said tank, and for calculating the reduction in liquid load during said elapsed time to determine the average flow rate out of said tank during said elapsed time.

8. A liquid volume gauge as defined in claim 6, wherein said sensor-transducer further comprises:

a mechanical structure around said magnetostrictive element;

a compressive device mounted on said mechanical structure for exerting an adjustable compressive load on said magnetostrictive element to establish initial conditions of compressive stress in said magnetostrictive element to ensure repeatable operation for extended periods of use.

9. A liquid volume gauge as defined in claim 8, wherein:

said compressive device includes a screw threaded into a hole in said mechanical structure and axially aligned with said primary axis of action, whereby said screw can be torqued down to apply compressive load on said magnetostrictive element to establish said initial conditions of compressive stress therein.

10. A method of operating a magnetostrictive transducer and measuring the liquid volume of a tank having a dynamic structural resonant frequency that varies with the liquid volume held by said tank, comprising:

applying an electrical signal to an excitation coil wound on a magnetostrictive element having a primary axis of action, said excitation coil having a coil axis substantially aligned with said axis of action, for applying a magnetic field, representative of a desired action of said transducer, to said magnetostrictive element;

applying a bias current to a bias coil wound around a magnetostrictive element in said transducer, with said bias coil having an axis aligned with the primary axis of action of said magnetostrictive element, to provide a magnetic field for establishing initial conditions of magnetic flux in a magnetic circuit through said magnetostrictive element to ensure repeatable operation of said transducer for extended periods of use;

transmitting to said tank mechanical vibrations induced in said magnetostrictive element by said magnetic field arising from said electrical signal in said excitation coil;

measuring the dynamic structural resonant frequency of said tank loaded by said liquid in said tank;

producing dynamic electrical resonant signals indicative of said dynamic structural resonant frequency;

translating said dynamic resonance signals into signals indicative of said liquid load in said tank;

conducting said liquid load indicating signals to a display; and displaying the volume of said liquid load in said tank.

11. A method of operating a magnetostrictive transducer as defined in claim 10, comprising:

exerting an adjustable compressive load on said magnetostrictive element with a compressive device mounted on a mechanical structure around said magnetostrictive element to establish initial conditions of compressive stress in said magnetostrictive element to ensure repeatable operation for extended periods of use.

12. A method of operating a magnetostrictive transducer as defined in claim 11, wherein said step of exerting a compressive load includes:

torquing down a screw threaded into a hole in said mechanical structure and axially aligned with said primary axis of action to apply compressive load on said magnetostrictive element to establish said initial conditions of compressive stress therein.

13. A method as defined in claim 10, further comprising:

comparing a liquid load in said tank at a start time with a liquid load after a certain period of time has elapsed from said start time, during which time liquid has flowed out of said tank at an average flow rate causing a reduction in liquid load in said tank; and calculating said reduction in liquid load during said elapsed time to determine said average flow rate out of said tank during said elapsed time.

* * * * *